United States Patent [19]

Kenney et al.

[11] Patent Number: 5,739,037
[45] Date of Patent: Apr. 14, 1998

[54] PROCESS FOR ELIMINATING LABILE GLYCOHAEMOGLOBIN FROM A SAMPLE

[75] Inventors: Andrew C. Kenney, Marlow; Maria D. Adewunmi, London, both of United Kingdom

[73] Assignee: Drew Scientific Limited, United Kingdom

[21] Appl. No.: 791,473

[22] Filed: Jan. 27, 1997

Related U.S. Application Data

[63] Continuation of Ser. No. 406,878, filed as PCT/GB93/02019, Sep. 28, 1993 published as WO94/08242, Apr. 14, 1994, abandoned.

[30] Foreign Application Priority Data

Sep. 29, 1992 [GB] United Kingdom ............... 9220526

[51] Int. Cl.$^6$ ................................................ G01N 33/72
[52] U.S. Cl. .......................... 430/67; 436/15; 436/17; 436/18; 436/66; 436/175; 530/385
[58] Field of Search ................... 436/15, 17, 18, 436/66, 67, 175; 530/385

[56] References Cited

U.S. PATENT DOCUMENTS

| | | | |
|---|---|---|---|
| 4,297,238 | 10/1981 | Vormbroch et al. | 436/17 |
| 4,376,727 | 3/1983 | Sato et al. | 200/112 B |
| 4,407,961 | 10/1983 | Sanders | 436/67 |
| 4,409,335 | 10/1983 | Hanamoto et al. | 436/67 |
| 4,438,204 | 3/1984 | Deeg et al. | 436/67 |
| 4,780,419 | 10/1988 | Uchida et al. | 436/18 |
| 4,831,012 | 5/1989 | Estep | 514/6 |
| 4,861,867 | 8/1989 | Estep | 530/385 |
| 4,879,039 | 11/1989 | Takahashi et al. | 210/635 |
| 4,925,574 | 5/1990 | Hsia | 210/635 |
| 5,004,546 | 4/1991 | Takahashi et al. | 210/635 |
| 5,169,932 | 12/1992 | Smith | 530/385 |
| 5,227,305 | 7/1993 | Manzoni et al. | 436/19 |
| 5,292,663 | 3/1994 | Yamazaki et al. | 436/67 |
| 5,304,491 | 4/1994 | Chiang et al. | 436/15 |
| 5,320,965 | 6/1994 | Chiang | 436/15 |
| 5,447,612 | 9/1995 | Bier et al. | 204/182.8 |
| 5,453,379 | 9/1995 | Yamazaki et al. | 436/67 |
| 5,474,677 | 12/1995 | Naka | 436/67 |
| 5,541,117 | 7/1996 | Karl et al. | 436/66 |
| 5,589,393 | 12/1996 | Fiechtner et al. | 436/15 |

FOREIGN PATENT DOCUMENTS

| | | |
|---|---|---|
| 0 255 122 2 | 3/1988 | European Pat. Off. . |
| 0 271 713 A2 | 6/1988 | European Pat. Off. . |

OTHER PUBLICATIONS

Chemical Abstracts, vol. 107, No. 3, 20 Jul. 1987, Columbus, Ohio, US; Abstract No. 20313.

Chemical Abstracts, vol. 117, No. 15, 12 Oct. 1992, Columbus, Ohio, US; Abstract No. 146718.

"Data for Biochemical Research" pp. 421, 424 and 425, Dawson et al, Third Edition (no date).

*Primary Examiner*—Jill Warden
*Assistant Examiner*—Sharidan Carrillo
*Attorney, Agent, or Firm*—Nixon & Vanderhye

[57] ABSTRACT

A process for the elimination of labile glycohaemoglobin from a sample comprises adding to the sample a reagent comprising a temperature dependent buffer having a pH/temperature coefficient of −0.011 or less, and a method for measuring the concentration of stable glycohaemoglobin in sample containing stable and labile glycohaemoglobin fractions.

14 Claims, 3 Drawing Sheets

PROCESS FOR ELIMINATING LABILE GLYCOHAEMOGLOBIN FROM A SAMPLE

CROSS-REFERENCES TO RELATED APPLICATIONS

This application is a continuation of application Ser. No. 08/406,878, filed May 17, 1995, now abandoned, which is a 371 of PCT/GB93/02019, filed Sep. 28, 1993, published as WO94/08242, Apr. 14, 1994.

BACKGROUND OF THE INVENTION

1. Field of the Invention

The present invention relates to a process for the elimination of labile glycohaemoglobin from a sample prior to measurement of glycohaemoglobin.

The measurement of glycohaemoglobin in blood samples is widely used because its levels are indicative of long-term blood glucose concentration. Measurement of glycohaemoglobin is useful in the treatment and control of conditions where a knowledge of the blood glucose concentration is important, for example, hyperglycaemia.

Glycohaemoglobin (HbA1c) is formed by the non-enzymic reaction of glucose with haemoglobin (HbAO). The reaction proceeds in two steps. The first step is the fast, reversible formation of a Schiff's base. The second step is a slow, irreversible Amadori rearrangement leading to the HbA1c adduct. The Schiff's base intermediate (known as the "labile fraction" of HbA1c or "pre-HbA1c") is very similar chemically to stable HbA1c and it interferes with measurement of HbA1c because it is difficult to resolve the two forms by most techniques, for example, chromatography. This leads to uncertainty as to the amount of stable glycohaemoglobin present.

To prevent the labile fraction interfering with the measurement of stable HbA1c, it is necessary substantially to reduce the labile fraction to an insignificant level prior to analysis. This is usually accomplished by driving the reversible reaction, by which the Schiff's base intermediate is formed, backwards to form glucose and haemoglobin. A number of methods have previously been used to do this. These include incubation (of erythrocytes) with normal saline and incubation (of erythrocytes) at pH5 with semicarbazide/aniline.

It is known, for example, that lowering the pH leads to the elimination of labile HbA1c. However, at the values of pH at which this proceeds quickly, the haemoglobin is stable for only a short period.

It is also known that the rate of labile HbA1c elimination may be increased by heating of the sample, but this has the drawback that prolonged heating causes the sample to deteriorate. A method currently employed in the applicant's laboratory is to eliminate the labile fraction by the addition of a haemolysing solution (pH 6.0) to the sample which is then left for either two hours at room temperature (standard method) or for thirty minutes at 37° C. This has been found to minimise damage to the sample but does not completely overcome this difficulty and is inconvenient and expensive due to the prolonged reaction times.

SUMMARY OF THE INVENTION

The present invention allows labile HbA1c to be eliminated quickly and easily from a sample and is achieved using only a single reagent without substantially affecting the stability of the sample.

Accordingly, the present invention provides a process for the elimination of labile glycohaemoglobin from a sample which process comprises adding to the sample a reagent comprising a temperature dependent buffer having a pH/temperature coefficient of −0.011 or less, the reagent being added at a temperature of up to 65° C. at which the buffer has a pH of less than 6.0 and reducing the temperature of the mixture such that the pH increases to 5.5 or more. Typically, the reagent is added to the sample at a temperature of up to 56° C.

Under the conditions of low pH and elevated temperature at which the reagent is added the elimination of labile glycohaemoglobin is rapidly accomplished. Immediately after addition of the reagent, unless steps are otherwise taken, the sample begins to cool. Due to the negative temperature coefficient of the buffer, as the sample cools, the pH is raised so that sample stability is preserved.

The reagent is heated to a temperature at which the pH of the reagent is less than 6.0, preferably from 5.0 to 5.5. No additional benefit is observed when the pH is lower than 5.0 and at and above 6.0 the stability of the labile fraction is increased so that the removal rate is too slow.

The temperature at which the reagent is added is about 65° C. or less, preferably 37° to 65° C., for example 37° to 56° C. At a temperature in excess of about 65° C. there is a greatly increased risk that the haemoglobin will be damaged or destroyed, whereas the pH reduction at less than 37° C. is small and the duration of reaction is too long. The final temperature and pH are selected with a view to the stability of the sample, particularly if it is to be stored prior to analysis. A pH of 5.5 at a temperature of 25° C. or less will generally afford adequate stability, but preferably a pH of 6.0 or above is achieved.

The buffer must have a sufficiently negative pH/temperature coefficient ($pK_a/°C.$) to provide a low pH at the addition temperature and to revert to a pH at which the HbA1c is stable on cooling and thus has a pH/temperature coefficient of −0.011 or less, preferably −0.015 or less, in particular about −0.018.

There is no particular lower limit on the pH/temperature coefficient imposed by the process and buffers having coefficients of −0.030 or less are available.

Suitable temperature-dependant buffers are well known to those skilled in the art and are based on complex secondary or tertiary amines. Originally described by N. E. Good et al. [Biochemistry, 5, 467 (1966)], they have become known as "Good" buffers.

Examples of suitable buffers include bis(2-hydroxyethyl)imino-tris(hydroxymethyl)methane ($pK_a/°C.=-0.018$);

2-(N-morpholino)ethanesulphonic acid ($pK_a/°C.=-0.011$);

N-(2-acetamido)imino diacetic acid ($pK_a/°C.=-0.011$);

N-(2-acetamido)-2-aminoethanesulphonic acid ($pK_a/°C.=-0.020$);

2-aminoethyl-trimethylammonium chloride hydrochloride ($pK_a/°C.=-0.027$ as the chloride), N,N-bis(2-hydroxyethyl)-2-aminoethanesulphonic acid ($pK_a/°C.=-0.016$), N,N-bis(2-hydroxyethyl)glycine ($pK_a/°C.=-0.018$), 2-(cyclohexylamino)ethanesulphonic acid ($pK_a/°C.=-0.011$) , N-2-hydroxyethylpiperazine-N'-2-ethanesulphonic acid ($pK_a/°C.=-0.014$).

N-2-hydroxyethylpiperazine-N'-3-propanesulphonic acid ($pK_a/°C.=-0.011$),

N-glycylglycine ($pK_a/°C.=-0.028$), 3-(N-morpholino)propanesulphonic acid ($pK_a/°C.=-0.011$), tris(hydroxymethyl)methylamine ($pK_a/°C.=-0.031$), tris(hydroxymethyl)methylammonium chloride ($pK_a/°C.=-0.031$)

N-tris(hydroxymethyl)methyl-2-aminoethanesulphonic acid ($pK_a/°C.=-0.020$) and

N-tris(hydroxymethyl)methylglycine ($pK_a/°C.=-0.021$).

By way of example, if it is desired to add the reagent at 56° C. and pH 5.5 and to achieve a pH of 6.0 on cooling to 25° C., a buffer having a pH/temperature coefficient of about −0.018 is required.

Particularly preferred is bis(2-hydroxyethyl)imino-tris(hydroxyethyl)methane.

Preferably the reagent used in the present invention is a haemolysing reagent containing the temperature dependant buffer, optionally also containing conventional additional haemolysing materials such as saponin, and suitable antimicrobials or preservatives such as sodium azide. In practice the haemolysing reagent will be maintained at a suitable temperature, such as 56° C., and added to samples as required. Samples will normally be aliquots of whole blood freshly taken from patients.

Elimination of the labile fraction is a complex function of temperature, incubation time and pH. The target is an elimination time of less than 15 minutes, preferably less than 10 minutes, particularly about 5 minutes, without compromising the long term stability of the sample. Shorter reaction times can be achieved by using higher temperatures, lower pH or both within the foregoing limits and by maintaining the mixture at the addition temperature then rapidly cooling rather than simply allowing the mixture to cool naturally.

The buffer, addition temperature, cooling and final temperature will be selected in order to achieve a desired duration of reaction affording sufficient elimination of the labile fraction whilst preserving the stability of the sample which may readily be determined by simple experiments.

The present invention also provides a method of measuring the concentration of stable glycohaemoglobin in a sample comprising both stable and labile fractions which comprises eliminating labile glycohaemoglobin from the sample by the process defined above and then measuring the concentration of stable glycohaemoglobin. Measurement may be by conventional techniques. Preferably the mixture is cooled to the temperature at which measurement of glycohaemoglobin concentration is to take place, for instance about 25° C. In such a case, analysis of the sample may be commenced immediately.

The final temperature and pH of the mixture will generally be selected having regard to the stability of the sample, as discussed above, and the conditions under which the HbA1c content is to be analysed. Thus, in the Example below, a Glycomat haemoglobin analyser (Ciba Corning Diagnostics Ltd) is used. This has an ion exchange column equilibrated at pH 6.2 and samples are loaded at 25° C. In this case the lowest pH which can be accommodated whilst obtaining good performance is pH 6.0. In other systems the final values of pH and temperature may be different.

Preferably the reagent is prepared and the pH adjusted to take into account the conditions of temperature and pH at which measurement of the glycohaemoglobin is to take place. The pH may be adjusted by the addition of a suitable acid, for example concentrated hydrochloric acid, so that the pH at the temperature at which analysis takes place is suitably controlled. If pH adjustment is undertaken at any other temperature, the target pH value may be calculated by use the pH/temperature coefficient of the buffer. For example, in the Example below, the pH of the haemolysing reagent is adjusted so that at 25° C. a pH of 6.0 will be achieved. For this, accurate measurement of temperature is required.

DESCRIPTION OF THE PREFERRED EMBODIMENTS

The following Examples illustrate the invention but are not intended to limit the extent of protection.

In FIGS. 1 to 5 referred to in the Examples % HbA1c refers to the concentration of measurable glycohaemoglobin of stable and, where present, liable glycohaemoglobin.

EXAMPLE 1

Rate of labile fraction removal at 56° C.

Bis(2-hydroxyethyl)imino-tris(hydroxymethyl)methane, (0.836 g, 40 mM, Sigma Chemical Co.), Saponin from *Gypsophilia sp.* (5 mg, Sigma Chemical Co.) and sodium azide (20 mg, Sigma Chemical Co.) were dissolved in deionised water (80 ml) and titrated with concentrated hydrochloric acid (Fisons) so that the pH at 25° C. was 6.0. Deionised water was added to make the volume up to 100 ml. The solution was left to stand for 2 hours after which the pH was readjusted. The haemolysing reagent was then heated to the experimental temperature (56° C.).

Samples (20 μl) of fresh human blood anticoagulated with ethyl diamine tetracetic acid (EDTA) were pipetted into microcentrifuge tubes (Glycomat sample vials in a Glycomat Autoloader rack).

Haemolysis and labile fraction elimination were initiated by adding heated haemolysing reagent (1 ml) to the samples using a dispenser pipette. Following addition of the heated haemolysing reagent the blood samples were allowed to cool to room temperature. Analysis for HbA1c took place at approximately 5 minutes after addition of the haemolysing reagent using a Glycomat haemoglobin analyzer (Ciba Corning Diagnostics Ltd) equipped with Glycomat Blue Fast HbA1c reagent kits (Ciba Corning Diagnostics Ltd.) for 5 minute HbA1 (labile)/HbA1c assays according to the manufacturers instructions.

The amount of glycohaemoglobin in the samples was about 6% of total haemoglobin and did not change significantly when retested at 5 minute intervals over 100 minutes showing that the content of labile fraction is rapidly and substantially reduced at 56° C.

EXAMPLE 2

Rate of labile fraction removal at 20°, 50°, 60° and 65° C.

Example 1 was repeated for haemolysing reagent temperatures of 20°, 50°, 60° and 65° C. The amount of glycohaemoglobin in the samples was measured over a 30 minute period. The results obtained are expressed graphically in FIG. 1.

Figure 1:
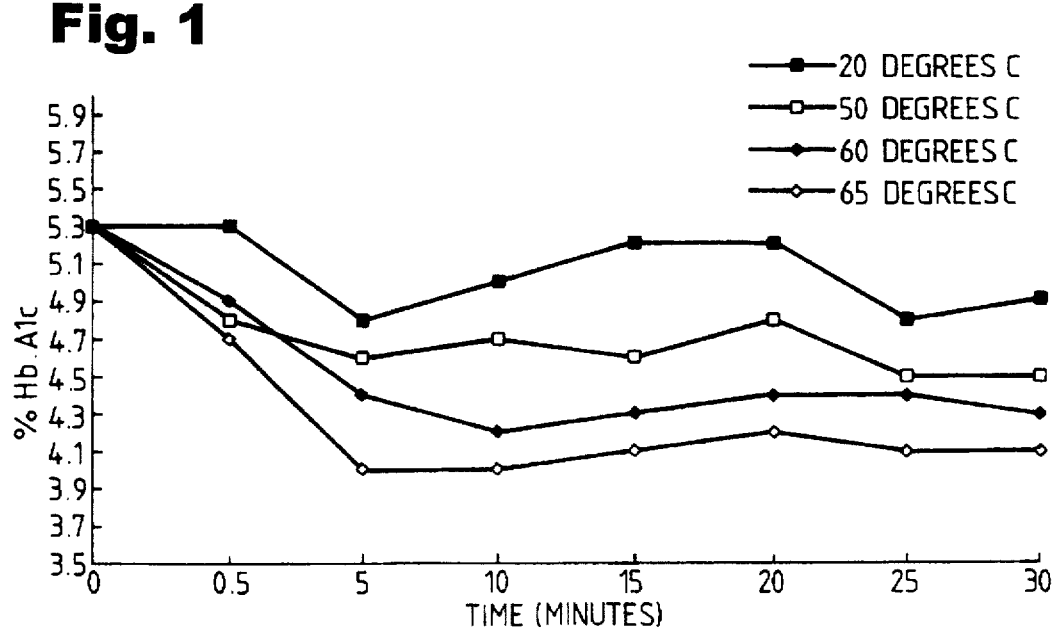
FIG. 1 shows the rate of labile fraction removal at 20°, 50°, 60°, and 65° C.

FIG. 1 shows that increasing the temperature at which the haemolysing reagent is added increases the rate of removal of labile glycohaemoglobin. The most rapid reduction in the percentage of measurable glycohaemoglobin (and thus the most rapid elimination of the labile fraction) between 0 and 5 minutes occurs at a haemolysing reagent temperature of 65° C.

The figure also shows that for a haemolysing reagent temperature of 65° C. the amount of measurable glycohaemoglobin remains effectively constant at times in excess of 5 minutes. This means that at this temperature all of the labile glycohaemoglobin is eliminated from the sample in under 5 minutes.

EXAMPLE 3

Removal of glycated haemoglobin at 20° and 60° C.

Figure 2:
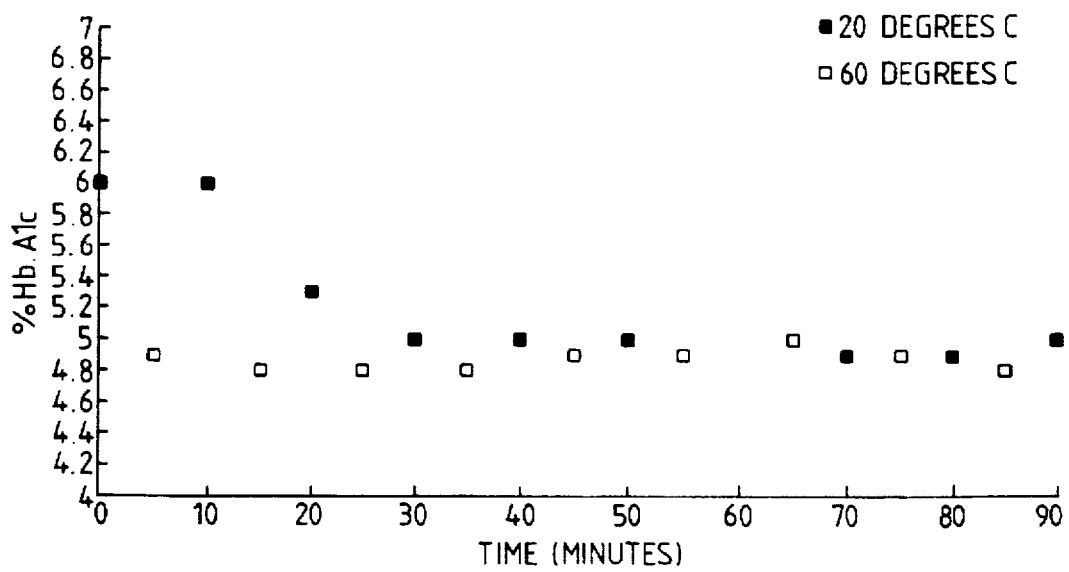
FIG. 2 shows the removal of glycated haemoglobin at 20° and 60° C.

Example 1 is repeated for haemolysing reagent temperatures of 20° and 60° C. over a period of 90 minutes. The results obtained are shown in FIG. 2.

At 60° C. the removal of the labile glycohaemoglobin fraction occurs much more rapidly than at ambient temperature (20° C.). The percentage of measurable glycohaemoglobin reached an equilibrium value after only about 5 minutes for a haemolysing reagent temperature of 60° C., whereas at 20° C. the equilibrium value was not reached until in excess of 60 minutes. This equilibrium value corresponds to the proportion of stable glycohaemoglobin in the sample, the labile fraction having been eliminated.

EXAMPLE 4

Removal of labile glycated haemoglobin at pH5, 6 and 7

Bis(2-hydroxyethyl)imino-tris(hydroxymethyl)methane, (0.836, g Sigma Chemical Co.), Saponin from *Gypsophilia sp.* (5 mg, Sigma Chemical Co.) and sodium azide (20 mg, Sigma Chemical Co.) were dissolved in deionised water (80 ml) and titrated with concentrated hydrochloric acid (Fisons) to the appropriate pH (5.0, 6.0 or 7.0) at 25° C. Deionised water was added to make the volume up to 100 ml. The solution was left to stand for 2 hours after which the pH was readjusted.

Samples (20 µl) of fresh human blood anticoagulated with ethyl diamine tetracetic acid (EDTA) were pipetted into microcentrifuge tubes (Glycomat sample vials in a Glycomat Autoloader rack).

Figure 3:
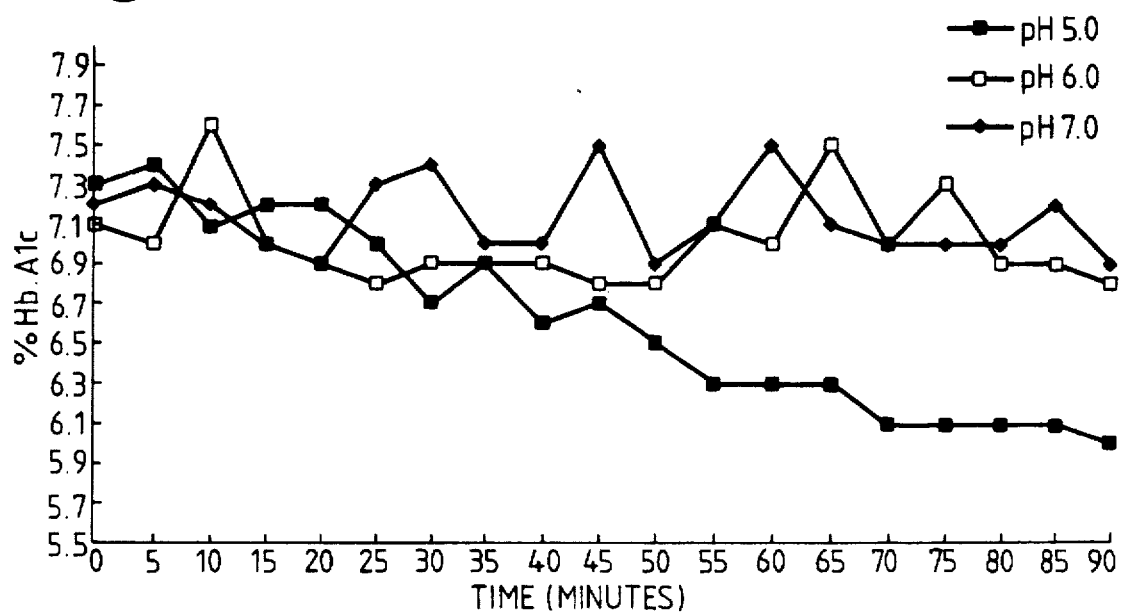
FIG. 3 shows the removal of labile glycated haemoglobin at pH 5, 6, and 7.

The haemolysing reagent is added to the blood samples at 25° C. and then analysed for HbA1c at approximately 5 minutes thereafter by the same procedure as in Example 1. The results are shown in FIG. 3.

At ambient temperature the time taken to a reach the equilibrium value of measurable glycohaemoglobin increases with increasing pH. As it is known that elimination of labile glycohaemoglobin proceeds more rapidly at low pH it can be concluded that rapid removal of labile glycohaemoglobin can only be achieved using a combination of low pH (below 6.0) and high temperature.

EXAMPLE 5

Stability of sample glycohaemoglobin with time

Figure 4:
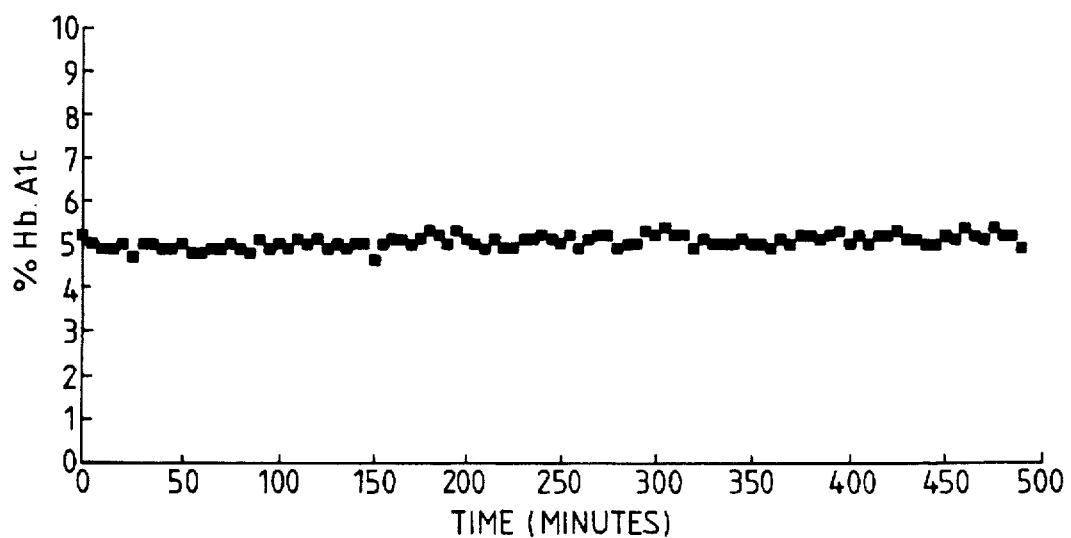
FIG. 4 shows the glycohaemoglobin concentration over a period of 500 minutes.

The procedure of Example 1 was repeated using a haemolysing reagent temperature of 65° C. corresponding to a pH of approximately 5.3. Measurement of glycohaemoglobin concentration took place over a period of 500 minutes. The results obtained are shown in FIG. 4.

The data in the figure confirm that the amount of measurable glycohaemoglobin remains constant even when the sample is exposed to extremes of pH and temperature. The method of the invention exposes the sample to these conditions only transiently and this has the advantage of preserving sample integrity.

EXAMPLE 6

Comparison of the method of the invention with standard method

Figure 5:
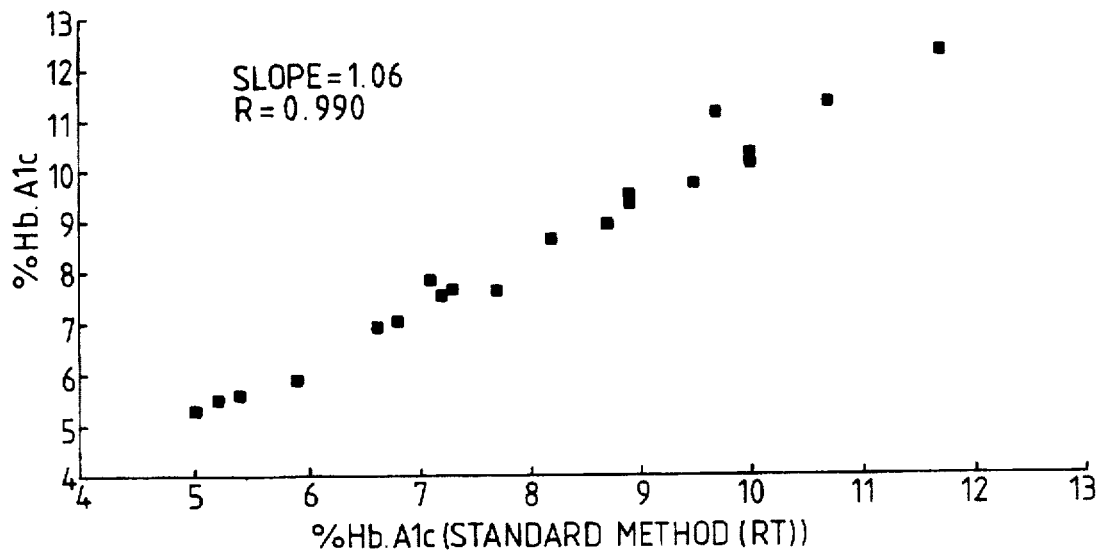
FIG. 5 shows regression analysis of data obtained from Example 1.

A regression analysis is performed on data obtained using the standard method referred to earlier (a haemolysing solution of pH 6.0 at room temperature for two hours) and data obtained using the procedure of Example 1 for a haemolysing reagent temperature of 65° C. The results are shown in FIG. 5.

The figure is a plot of equilibrium glycohaemoglobin concentration obtained using the standard method versus the equilibrium glycohaemoglobin concentration obtained by the present method for a number of samples having different initial glycohaemoglobin (stable plus labile) concentrations.

The correlation coefficient, R, is equal to 0.990 showing that methods correlate well, and can therefore be considered equivalent in terms of data accuracy.

EXAMPLE 7

Effect of temperature on haemolysing reagent pH

Figure 6:
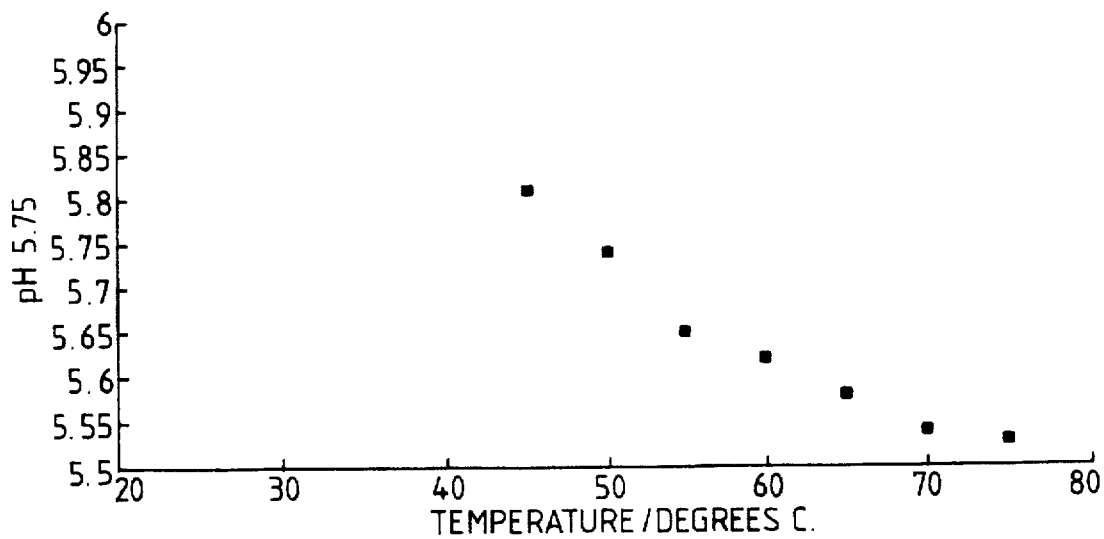
FIG. 6 shows the effect of temperature on haemolysing reagent pH.

The effect of temperature on the pH of the haemolysing reagent of Example 1 is investigated. The results are shown in FIG. 6.

Increasing the temperature of the haemolysing reagent is accompanied by a reduction in the pH. The type of plot shown in FIG. 6 may be used as a calibration curve for a given buffer contained in the haemolysing reagent to identify what temperature should be employed to obtain a particular pH.

What is claimed is:

1. A process for preparing a sample for glycohaemoglobin measurement, which process comprises adding a reagent to said sample thereby forming a mixture, said reagent comprising a temperature dependent buffer having a pH/temperature coefficient of −0.011 or less, said reagent being added to said sample at a first temperature of up to 65° C., at which at said first temperature, said buffer has a first pH of less than 6.0, incubating the reagent with the sample, and allowing the temperature of said mixture to change to a second temperature, which is lower than said first temperature, whereby the temperature change causes the pH of said buffer to change to a second pH of 5.5 or more, said second pH being higher than said first pH, said first temperature and said first pH causing elimination of labile glycohaemoglobin from said sample.

2. A process according to claim 1, wherein the temperature at which the reagent is added is from 37° to 65° C.

3. A process according to claim 1, wherein the pH at which the reagent is added is from 5.0 to 5.5.

4. A process according to claim 1, wherein the temperature of the mixture is reduced such that the pH increases to 6.0 or more.

5. A process according to claim 1, wherein the temperature dependent buffer is:

bis(2-hydroxyethyl)imino-tris(hydroxymethyl)methane;

2-(N-morpholino)ethanesulphonic acid;

N-(2-acetamido)imino diacetic acid;

N-(2-acetamido)-2-aminoethanesulphonic acid;

2-aminoethyl-trimethylammonium chloride hydrochloride;

N,N-bis(2-hydroxyethyl)-2-aminoethanesulphonic acid;

N,N-bis(2-hydroxyethyl)glycine;

2-(cyclohexylamino)ethanesulphonic acid;

N-2-hydroxyethylpiperazine-N'-2-ethanesulphonic acid;

N-2-hydroxyethylpiperazine-N'-3-propanesulphonic acid;

N-glycylglycine;

3-(N-morpholino)propanesulphonic acid;

tris(hydroxymethyl)methylamine;

tris(hydroxymethyl)methylammonium chloride;

N-tris(hydroxymethyl)methyl-2-aminoethanesulphonic acid; or

N-tris(hydroxymethyl)methylglycine.

6. A process according to claim 1, wherein the temperature dependent buffer has a pH/temperature coefficient of −0.015 or less.

7. A process according to claim 6, wherein the temperature dependent buffer has a pH/temperature coefficient of −0.018.

8. A process according to claim 7, wherein the pH temperature dependent buffer is bis(2-hydroxyethyl)imino-tris(hydroxymethyl)methane.

9. A process according to claim 1, wherein the reagent is incubated with the sample for less than 15 minutes.

10. A process according to claim 9, wherein the reagent is incubated with the sample for less than 10 minutes.

11. A process according to claim 10, wherein the reagent is incubated with the sample for about 5 minutes.

12. A process according to claim 1, wherein the reagent is a haemolysing reagent containing the temperature dependent buffer.

13. A process according to claim 12, wherein the reagent further contains saponin.

14. A process according to claim 13, wherein the reagent further contains an antimicrobial agent or preservative.

* * * * *